(12) United States Patent
Reyes Montaño et al.

(10) Patent No.: US 11,661,440 B2
(45) Date of Patent: May 30, 2023

(54) SYNTHETIC PEPTIDES THAT MODULATE THE NMDA RECEPTOR

(71) Applicants: Edgar Antonio Reyes Montaño, Bogotá (CO); Edwin Alfredo Reyes Guzmán, Bogotá (CO); Nohora Angélica Vega Castro, Bogotá (CO)

(72) Inventors: Edgar Antonio Reyes Montaño, Bogotá (CO); Edwin Alfredo Reyes Guzmán, Bogotá (CO); Nohora Angélica Vega Castro, Bogotá (CO)

(73) Assignee: Universidad Nacional de Colombia, Bogota (CO)

( * ) Notice: Subject to any disclaimer, the term of this patent is extended or adjusted under 35 U.S.C. 154(b) by 129 days.

(21) Appl. No.: 17/145,492

(22) Filed: Jan. 11, 2021

(65) Prior Publication Data

US 2021/0130407 A1   May 6, 2021

Related U.S. Application Data

(60) Continuation of application No. 16/909,984, filed on Jun. 23, 2020, now abandoned, which is a division of application No. 16/065,078, filed as application No. PCT/IB2016/057956 on Dec. 22, 2016, now Pat. No. 10,689,418.

(30) Foreign Application Priority Data

Dec. 22, 2015   (CO) .................... 15-303915

(51) Int. Cl.
*C07K 7/08*      (2006.01)
*A61K 38/00*    (2006.01)

(52) U.S. Cl.
CPC ............... *C07K 7/08* (2013.01); *A61K 38/00* (2013.01)

(58) Field of Classification Search
None
See application file for complete search history.

*Primary Examiner* — Sergio Coffa
(74) *Attorney, Agent, or Firm* — Isaacs Angres

(57) ABSTRACT

The invention provides a series of peptides with N-methyl-D-aspartate (NMDA) receptor modulating activity. Specifically it contains two synthetic peptides acting as ion inflow antagonists through the NMDA receptor with specificity GluN2B and GluN2A NMDA receptor subunits and a peptide having agonist activity regarding the NMDA receptor in rat hippocampal neuron cultures.

4 Claims, 9 Drawing Sheets

Specification includes a Sequence Listing.

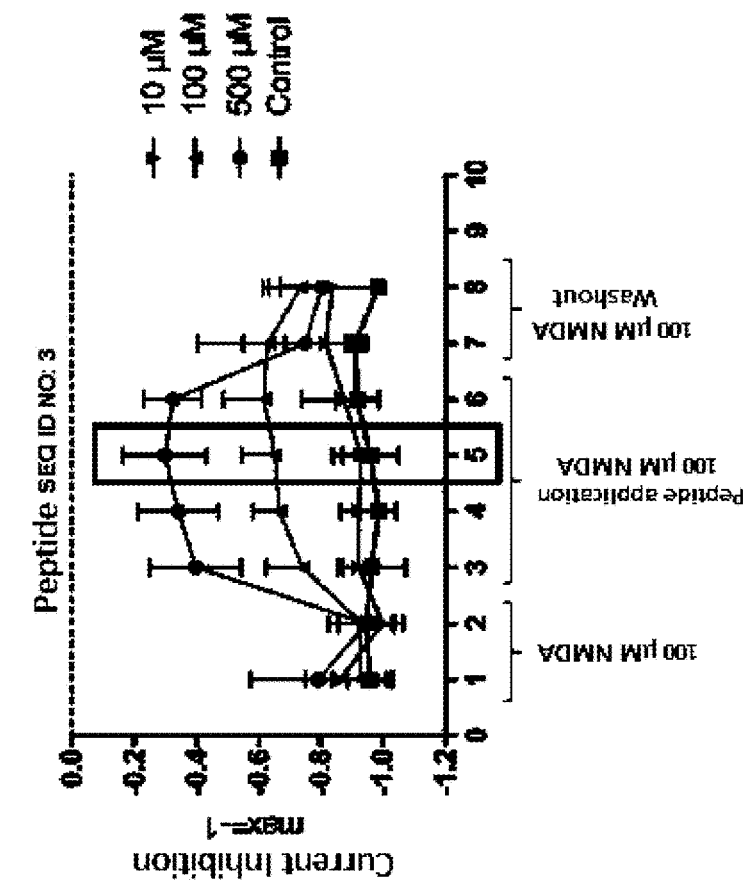
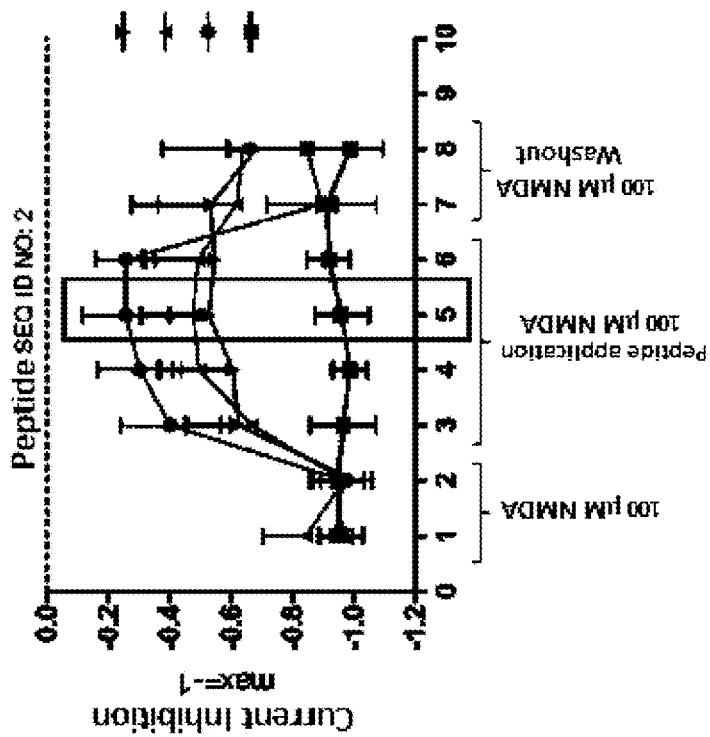

SYNTHETIC PEPTIDES THAT MODULATE THE NMDA RECEPTOR

This application is a continuation of pending U.S. application Ser. No. 16/909,984 filed Jun. 23, 2020; which application is a divisional of U.S. application Ser. No. 16/065,078 filed Jun. 21, 2018, now U.S. Pat. No. 10,689,418 issued Jun. 23, 2020; which application is a 371 application of International Application No. PCT/IB2016/057956 filed Dec. 22, 2016; (published on Jun. 29, 2017 as (WO/2017/109756) titled "Synthetic Peptides that Modulate the NMDA Receptor"; the entire contents of which are hereby incorporated by reference herewith. This application also claims priority to CO Application No. 15-303915 filed Dec. 22, 2015.

FIELD OF THE INVENTION

The invention described in this document is related to the field of peptides modulating N-methyl-D-aspartate (NMDA) receptor activity. It specifically refers to two synthetic peptides acting as ion inflow antagonists through the NMDA receptor and a peptide having agonist activity regarding the NMDA receptor in rat hippocampal neuron cultures.

BACKGROUND OF THE INVENTION

The N-methyl-D-aspartate (NMDAR) receptor is the main glutamate receptor subtype, usually participating in rapid excitatory synaptic transmission. These receptors are broadly expressed and have been implicated in physiological processes such as the neuron development, synaptic plasticity, memory and learning and many pathological conditions (Citri and Malenka, 2008). NMDAR has also been involved processes such as ischemic damage (Hardingham and Bading, 2010), chronic pain, psychosis, and the main degenerative disorders such as Parkinson's and Alzheimer's diseases (Mony et al., 2009a; Traynelis et al., 2010).

NMDA receptors are presented as a set of tetramers from two glycine binding GluN1 subunits and two glutamate binding subunits, of which there are four types (GluN2A, GluN2B, GluN2C and GluN2D). Both types of GluN2A and GluN2B subunits are considered the main elements for NMDA receptor functioning in central nervous system (CNS) neurons (Madden, 2002).

The GluN2 subunit controls a broad range of NMDA receptor functional properties and is differentially expressed throughout the whole CNS (Akazawa et al., 1994; Monyer et al., 1994). Each NMDA receptor subunit has four domains: the extracellular amino-terminal domain (ATD), the extracellular ligand binding domain (LBD), the transmembrane domain (TMD) and the intracellular carboxyl-terminal domain (CTD) (Sobolevsky et al., 2009).

Activating NMDA receptors requires two coincident events: glutamate and glycine binding and the simultaneous membrane depolarisation, thereby eliminating $Mg^{2+}$ channel pore-blocking, giving rise to $Ca^{2+}$ inflow. $Ca^{2+}$ inflow (in physiological conditions) produces partial inhibition of NMDA receptors through calcium-dependent inactivation, thereby impeding intracellular Ca2+ overload (Krupp et al., 1999). However, in pathological conditions such NMDA receptor regulation becomes deactivated, resulting in an excess of $Ca^{2+}$ inflow via the NMDA receptor, thereby triggering multiple intracellular catabolic processes and thus inducing neuron death (Lipton et al., 2006).

Given the NMDA receptor's complex functioning in synaptic transmission, memory and learning and the fact that it is highly implicated in pathological processes such as ischemic damage, pharmacology related to this receptor's regulation has been focused on testing antagonists directed against the glutamate binding site, the glycine binding site, the cannel in question ($Mg^{2+}$) and the receptor's allosteric regulatory sites, all as neuroprotective agents in many pre-clinical assays; however, such approaches have failed (Green, 2002; Parsons et al., 2002; Lo et al., 2003; Hoyte et al., 2004; Small and Tauskela, 2005; Wang and Shuaib, 2005; Muir, 2006). Regarding channel blocking agents (aptiganel, cerestat; CNS 1102) and the glutamate binding site, the levels of antagonism needed for producing/inducing neuroprotection affect cardiovascular function and alter cognition (psychotic effects) (Small and Tauskela, 2005; Muir, 2006). Gavestinel (GV150526), directed against the glycine binding site has also failed to provide the desired neuroprotection (Sacco et al., 2001). A selective antagonist from the GluN2B CP-101,606 subunit is apparently insufficient for protection against severe ischemic damage (Yurkewicz et al., 2005). Regarding other types of pathology, such as Alzheimer's and Parkinson's diseases, memantine has had promising results given its low affinity and rapid dissociation kinetics (classic antagonists lack such characteristics) (Kotermanski and Johnson, 2009).

Other types of antagonist derived from natural poisons have been tested against the NMDA receptor. Conotoxins are one such type of poisons, being small peptides produced by marine invertebrates from the genus *Conus*. These conotoxins are rigid protein compounds which are cysteine-rich (4-6 residues) in very well-defined positions and synthesised by a complex mechanism facilitating their great variability and efficiency in paralysing their prey, thereby guaranteeing this specie's evolutionary success (Olivera et al., 1997). The conotoxins have been characterised by having enormous specificity, binding to well-defined receptors on muscle or nerve cells where they act as ion channel antagonists, blocking their functionality.

The conantokins (one type of conotoxin) are small peptides (17-27 amino acids long), poor in disulphide bridges, differing from the other conotoxins; they are found in poison from *Conus geographus* and have high affinity for blocking the NMDA receptor and a potential anticonvulsant and antinociceptive effect (Layer et al., 2004; Xiao et al., 2008).

Conantokin-G (CGX-1007), or Con-G, is found within this group; it is a 17 amino acid-long peptide (GEγγLQγNQγLIRγKSN-NH2 (SEQ ID NO: 1)) which is characterised by having five modified gamma carboxyglutamate acid (γ-carboxyglutamic or Gla) amino acid residues. This toxin has competitive and non-competitive antagonism against NMDA receptor subunits (Prorok and Castellino, 2007). The γ-carboxyglutamic residues enable coordination of divalent ions (mainly Ca2+), thereby conferring α-helix structure on conantokin-G (Myers et al., 1990).

Various approaches involving conantokin-G analogous peptides, in which γ-carboxyglutamic residues have been partially and/or totally replaced by alanine and especially by glutamate (Lin et al., 1999; Chandler et al., 1993), have led to determining that conantokin-G antagonist activity against NMDA receptors depends strongly on amino-terminal residues where γ-carboxyglutamic residues play a structural and functional role, especially residues Gla3 and Gla4 (Blandl et al., 1998; Zhou et al., 1996; Warder et al., 1998). Along with γ-carboxyglutamic residues, conantokin-G Leucine 5 (Leu 5) its been described to be the determinant molecular allowing this toxin to have NMDA receptor GluN2B subunit LBD specificity (residue Met 739, located in LBD domain D2), thereby producing high selectivity and competitive antagonism against this subunit (Donevan and McCabe, 2000; Sheng et al., 2010).

The role of conantokin-G as antagonist of NMDA receptors has been evaluated in different scenarios. The rol of Conantokine-G as a NMDA receptor antagonist have been evaluated in different scenarios, boosting a large amount of patents. For instance, patent CA 2288346 A1 describes a method in which using Conantokine-G produces analgesia and neuroprotection when administered to mammals. U.S. Pat. No. 5,830,998A discloses a series of peptides base don modifications in N y C terminals of Conantokine-G and other peptides in which γ-carboxyglutamic residues are replaced with glutamate and the use as allosteric modulators of NMDA receptors in the central nervous System disorders treatment. U.S. Pat. No. 6,110,894A uses the same Conantokine-G derivates in the treatment of excitotoxicity produced by the stimulation of NMDA receptor during epilepsy episodes. Recently, patent request CN102167729A describes a Conantokine-G analogue (Glu-instead of-G) where the γ-carboxyglutamic residues are replaced with glutamate, showing an effect on the psychological and physical dependence on morphine; and compared to morphine the analogue has a stronger analgesic effect. It has been found that conantokin G has neuroprotective effects in an ischemic event and in staurosporin-induced apoptosis (Williams et al., 2002).

However, conantokin G's neuroprotective effect regarding an excitotoxic context, particularly concerning ischemia, has not been well established. A recent study concerning organotypic hippocampus cultures and in HEK293 cells expressing different combinations of NMDA receptor subunits (Alex et al., 2011), has highlighted conantokin G's neuroprotective effect in a excitotoxic environment. Conantokin acted as an effective GluN2B and GluN2A subunit blocker in the aforementioned study, suggesting that conantokin G is a potent molecule having a neuroprotective effect regarding an excitotoxic setting and that such effect is mediated by different NMDA receptor subunits, as opposed to previously described studies concerning conantokin-G selectivity for the GluN2B subunit.

Recent data have shown that Conantokine-G promotes neuronal integrity related neuroprotection and changes in the subunits cell location of the NMDA receptor in a in-vivo ischemia model (Balsara et al., 2015)

However, as the pre-clinic models using Conantokine-G as a NMDA receptor agonist to treat stroke have succeed, the pharmaceutic use has not been as expected (Balsara et al., 2012). For the treatment of seizures and epilepsy (Barton et al., 2004), Conantokine-G was proved with promising result in phase I, but failure in phase II of the clinical assays (obtained from a website called uniprot.org/uniprot/P07231, 2014)

As there is no effective pharmacological treatment for regulating the processes involved in NMDA-dependent pathologies that has been found to date, therefore the search for new pharmacotherapy drugs directed against the different sites modulated by the NMDA receptor must continue.

SUMMARY OF THE INVENTION

The present invention is related to the field of NMDA receptor activity modulating peptides. It specifically refers to two synthetic peptide antagonists derived from the conantokin-G sequence and an NMDA receptor peptide having agonist activity.

The first synthetic peptides presented in this invention has the following sequence GEDDLQDNQDLIRDKSN (SEQ ID NO: 2, given in the list of sequences), corresponding to the three letter code for the Gly-Glu-Asp-Asp-Leu-Gln-Asp-Asn-Gln-Asp-Leu-Ile-Arg-Asp-Lys-Ser-Asn sequence, ordered from the N-terminal to the C-terminal. The peptide has a 1975.03 g/mol molecular weight and is mainly hydrophilic and acidic.

The second synthetic peptide presented in this invention has the following sequence GEDDYQDAQDLIRDKSN (SEQ ID NO: 3, given in the list of sequences), corresponding to the three letter code for the Gly-Glu-Asp-Asp-Tyr-Gln-Asp-Ala-Gln-Asp-Leu-Ile-Arg-Asp-Lys-Ser-Asn sequence, ordered from the N-terminal to the C-terminal. The peptide has a 1981.99 g/mol molecular weight and is mainly hydrophilic and acidic.

Regarding the peptide presented as SEQ ID NO: 2 in this invention, the five modified gamma-carboxyglutamic amino acid residues in conantokin-G (positions 3, 4, 7, 10 and 14) have been replaced by aspartate (Asp), so that the whole SEQ ID NO: 2 sequence contains standard amino acids. The peptide presented as SEQ ID NO: 3; has the same modifications described for SEQ ID NO: 2; however, additional modification has involved Leu 5 having been substituted for Tyr, and Asn 8 for Ala.

The C-terminal residues for the peptides in SEQ ID NO: 2 and SEQ ID NO: 3 are not amidated as in conantokin-G.

For determining the effect which this new peptides (SEQ ID NO: 2; SEQ ID NO: 3) could have on NMDA receptor activity, an electrophysiological evaluation was made for analysing the changes in current evoked by the NMDA agonist and glycine coagonist in the NMDA receptor, in the absence and presence of peptides SEQ ID NO: 2 and SEQ ID NO: 3 (tested separately).

SEQ ID NO: 2 and SEQ ID NO: 3 peptide activity regarding the currents evoked by the NMDA receptor was evaluated by the patch clamp electrophysiological technique (Hamill et al., 1981) and whole-cell configuration, fixing voltage at −70 mV (clamp voltage) in an E18 Sprague Dawley rat embryo hippocampal neuron primary culture. NMDA receptor-evoked current was evaluated by using 100 µM NMDA and 10 µM glycine, in the absence and presence of peptides SEQ ID NO: 2 and SEQ ID NO: 3, at 10, 100 and 500 µM concentration. The peptide having the SEQ ID NO: 2 sequence had reduced concentration-dependent NMDA receptor inflow activity in hippocampal neuron cultures; likewise, the effect of peptide (SEQ ID NO: 2) did not alter recuperation of receptor activity by fresh applications of NMDA/glycine. Such data indicated an antagonist effect for peptide (SEQ ID NO: 2) on the NMDA receptor. For determining peptide (SEQ ID NO: 2) selectivity towards the main NMDA receptor GluN2 subunit subtypes, the NMDA receptor recombinant subunits (GluN1-a/GluN2A and GluN1-a/GluN2B) were independently expressed in HEK293 cells and the effect of input current was evaluated in the same way as that described for neurons. Peptide (SEQ ID NO: 2) had selectivity for the GluN1-a/GluN2B complex on GluN1-a/GluN2A, indicating that the peptide in this invention is selective and produces antagonism against the NMDA receptor GluN2B subunit, analogously to the antagonism known regarding conantokin-G.

The peptide presented as SEQ ID NO: 3 had concentration-dependent antagonism against the NMDA receptor in hippocampal neuron cultures, but not so marked, as peptide SEQ ID NO: 2. Regarding peptide SEQ ID NO: 3 selectivity towards NMDA receptor recombinant subunits, it was found that this peptide had antagonism against both types of subunit (GluN2A and GluN2B), indicating that Leu 5 and Asn 8 are important residues for discriminating between subunits.

Due to peptides GEDDLQDNQDLIRDKSN (SEQ ID NO: 2, 201.5 µM IC50) and GEDDYQDAQDLIRDKSN (SEQ ID NO: 3, 156.3 µM IC50) low affinity in neuron cultures for producing NMDA receptor antagonism, compared to reports regarding the affinity of classical NMDA receptor antagonists (Ogden and Traynelis, 2011), including conantokin-G (0.1 µM IC50, Teichert et al., 2007), the peptides presented here (SEQ ID NO: 2 and SEQ ID NO: 3) could represent interesting pharmacological potential due to high NMDA receptor dissociation and avoid the adverse effects associated with classical NMDA receptor antagonists.

Peptide KLGMRSELQIDNDQDAD (SEQ ID NO: 4) is also presented in this invention, its three letter code being: Lys-Leu-Gly-Met-Arg-Ser-Glu-Leu-Gln-Ile-Asp-Asn-Asp-Gln-Asp-Ala-Asp (ordered from the N-terminal to the C-terminal). This peptide has 1948.08 g/mol molecular weight, is mainly hydrophilic and is acid.

Electrophysiological evaluation of peptide SEQ ID NO: 4 in neuron culture revealed agonist activity for the NMDA receptor. Peptide SEQ ID NO: 4 evoked input current via the NMDA receptor at 500 µM concentration. This peptide is also presented as a pharmacological agent of interest regarding memory and learning where NMDA receptor activity must be maximised.

BRIEF DESCRIPTION OF THE FIGURES

FIG. 1A shows the input current (whole-cell) when using 100 µM NMDA and 10 µM glycine. The currents from left to right were obtained from the same neuron. The last graph of current shows merging between the first (black) and the last stimulation (grey). It can be observed that current magnitude was maintained as stimulations were made and no significant changes were seen regarding each current's deactivation kinetics. FIG. 1B shows inhibition of NMDA receptor-evoked currents using the (+)-MK801 antagonist on hippocampal neurons. The records of currents induced by using 100 µM NMDA and 10 µM glycine were significantly blocked due to (+)-MK801 antagonist occupation and permanence in the pore channel, indicating that, effectively, the currents were evoked by the NMDA receptor. FIG. 1C illustrates inhibiting NMDA receptor responses by the presence of subunit GluN2B using 1 µM Ro 25-968 for 10 seconds. The responses were evoked using 100 µM NMDA and 10 µM glycine for 5 seconds; 3-6 neurons were evaluated. 7-14 days in vitro (DIV).

FIGS. 2A and 2B illustrate that peptides having SEQ ID NO: 2 and SEQ ID NO: 3 had an antagonist effect against NMDA receptor-evoked currents on hippocampal neurons. The effects of 10, 100 and 500 µM peptide having SEQ ID NO: 2 is shown in FIG. 2A, and the effects of peptide SEQ ID NO: 3 is shown in FIG. 2B. The NMDA receptor-evoked currents (whole-cell) were obtained by using 100 µM NMDA and 10 µM glycine; the agonist was initially used twice (1-2, on the x (abscissa) axis), followed by four applications (3-6) of peptide and two applications of NMDA (7-8, washout) for evaluating recovery after the blocking; there was a 4-minute gap between each application. The currents were normalised regarding the largest application involving 100 µM NMDA and this was taken as maximum current (max=−1). Applications of 100 µM NMDA and 10 µM glycine were used as control; 4-7 neurons were evaluated per concentration.

FIG. 3A shows the effect 10 µM peptide having SEQ ID NO: 2. FIG. 3B illustrates the effect of 100 µM peptide having SEQ ID NO: 2. FIG. 3C describes the effect of 500 µM peptide having SEQ ID NO: 2. 100 µM NMDA and 10 µM glycine were used in all cases. Peptide and agonist residues were washed-out after each peptide application to remove and begin fresh stimulation with NMDA/glycine. The red lines show blocking by peptide SEQ ID NO: 2. The image at the end of each panel shows current merging. FIG. 3D shows the dose-response curve for peptide having SEQ ID NO: 2 regarding NMDA receptor-evoked currents. FIG. 3E shows the effect of 10 µM peptide having SEQ ID NO: 3. FIG. 3F illustrates the effect of of 100 µM peptide having SEQ ID NO: 3. FIG. 3G describes the effect of 500 µM peptide having SEQ ID NO: 3. FIG. 3H shows the dose-response curve for peptide having SEQ ID NO: 3 regarding NMDA receptor-evoked currents. The green lines show blocking by peptide having SEQ ID NO: 3. Currents for cells maintained with 2% bovine foetal serum (BFS) are shown for peptide having SEQ ID NO: 3. 4-7 cells were evaluated for each concentration. The peptides were evaluated independently.

FIG. 6A shows stimulation with 500 µM peptide having SEQ ID NO: 4 for 10 seconds in NMDA receptor-evoked currents (whole-cell) for 100 µM NMDA and 10 glycine. FIG. 6B shows the stimulation with 500 µM peptide having SEQ ID NO: 4 for 10 seconds produced an input current which was blocked by 10 µM (+)-MK-801.

DETAILED DESCRIPTION OF THE INVENTION

An electrophysiological evaluation of NMDA receptor macroscopic input current (evoked current) was made for ascertaining the effect of the synthetic peptides presented in the list of sequences as SEQ ID NO: 2, SEQ ID NO: 3 and SEQ ID NO: 4 on NMDA receptor activity in hippocampal neuron (7-14 DIV) cultures. Pharmacological treatment was used for blocking the activity of AMPA and kainate receptors, GABAA receptors, voltage-dependent glycine and sodium channels for isolating NMDA receptor currents, as explained in the Methodology section.

Figure 1A:
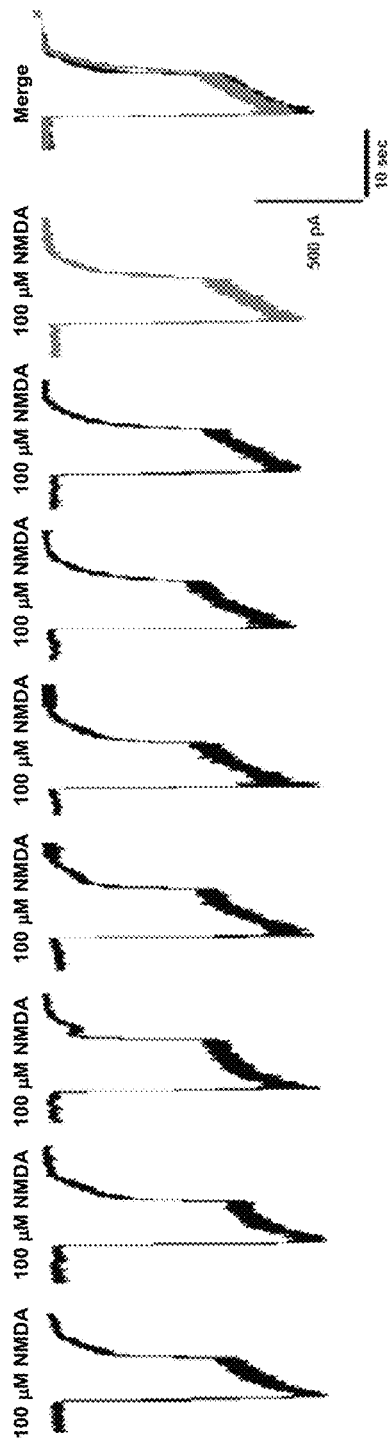
FIGS. 1A, 1B and 1C show the currents evoked by the NMDA receptor.

NMDA receptor-evoked currents were induced by using 100 μM NMDA (Sigma) and 10 μM glycine (Sigma) for 5 seconds; this was flowed by washing-out the agonists by perfusion with bath solution. Given the desensitisation of macroscopic currents which occurs with this type of channel (Nahum-Levy et al., 2001), successive stimulations were used at 4-minute intervals (this being the time needed for channel activity to recover), thereby allowing stable input current to be recorded at −60 mV fixed potential which was used as control (FIG. 1A).

Figure 1B:

The NMDA receptor selective and non-competitive antagonist (+)-MK-801 (dizocilpine, Tocris Bioscience) was used for ascertaining that the responses obtained were really produced by NMDA receptor stimulation; (+)-MK-801 acts by binding inside the (ion) pore channel, thereby preventing $Ca^{2+}$ inflow (Wong et al., 1986). Using 10 μM (+)-MK-801 provoked more than 50% reduction in the response obtained by stimulation with 100 μM NMDA and 10 μM glycine (FIG. 1B). A second application of (+)-MK-801 led to almost total blocking of the response and, in most cases, recovery of current after washing was not observed. These results indicated the presence of NMDA receptor-evoked currents.

Figure 1C:
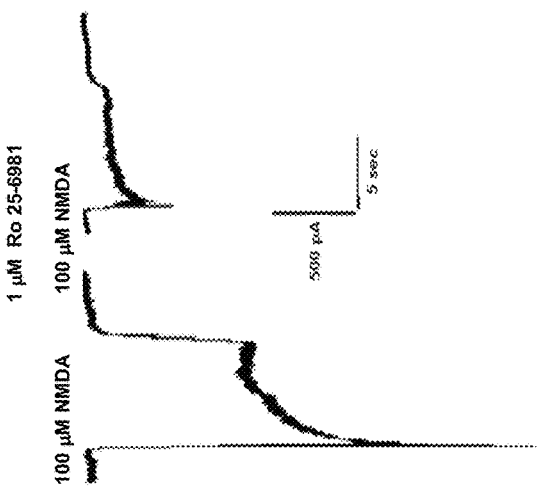

Due to the peptides presented in this invention being conantokin-G analogues and their molecular target the NMDA receptor GluN2B subunit, it was necessary to determine electrophysiologically the presence of the GluN2B subunit on different days in vitro. The Ro 25-9681 compound was used for this (a highly selective blocker depending on GluN2B activity) (Fischer et al., 1997). However, consecutive stimuli were needed when using 1 μM Ro 25-9681 to achieve less than 50% blocking of the response evoked when using 100 μM NMDA and 10 μM glycine (FIG. 1C). Ro 25-9681 has activity-dependent blocking and does not allow receptor activity to recover after blocking. Such responses were evaluated 7-14 DIV, significant blocking of the evoked responses being found, indicating the presence of subunit GluN2B in both young and mature in vitro cultures (Waxman and Linch, 2005).

A start was made on evaluating the designed peptides bearing in mind the presence of subunit GluN2B in the neurons on the aforementioned DIV. The changes in the magnitude of the NMDA agonist- and the coagonist glycine-evoked currents in the presence of the peptides would indicate an effect by the peptides being evaluated.

Electrophysiological Evaluation of the Peptides

Neurons were stimulated with NMDA and glycine to obtain an input current for a whole-cell patch clamp evaluation of the peptides mentioned in this invention, as shown in an earlier section, followed by using the peptides at different concentrations. Two NMDA/glycine applications were made, followed by four applications of the peptides at 4-minute intervals and then two more NMDA/glycine applications to ascertain recovery. The peptides were evaluated separately.

Peptide SEQ ID NO: 2 is a 17 amino acid-long peptide, mainly hydrophilic and acidic. Peptide stock solutions were prepared in aqueous solution; the peptide was added to the extracellular or bath solution using the same perfusion conditions as for the NMDA applications. Different peptide doses (10, 100 and 500 μM) were tested; the doses were also adjusted to 50 and 100 μM NMDA for evaluating whether it was NMDA receptor activity-dependent.

A significant reduction in current was not observed regarding stimulus at 50 μM NMDA at a dose of 10 μM peptide SEQ ID NO: 2 and, in some cases, the results indicated an increased response, something similar to what happens with Ro 25-9681 at very low doses (Fischer et al., 1997). When increasing NMDA concentration to 100 μM to see whether there had been any change in the effect of peptide SEQ ID NO: 2 at a concentration of 10 μM, a reduction in current of around 11±0.81% (n=10) was found. In some registers the inhibition was close to 40%, indicating that peptide SEQ ID NO: 2 could have been acting in an NMDA receptor activity-dependent fashion. It was also observed that peptide SEQ ID NO: 2 did not seem to be significantly altering receptor recovery after washing, in these conditions. Bearing the foregoing in mind, all the other responses involved using 100 μM NMDA.

Figure 3B:
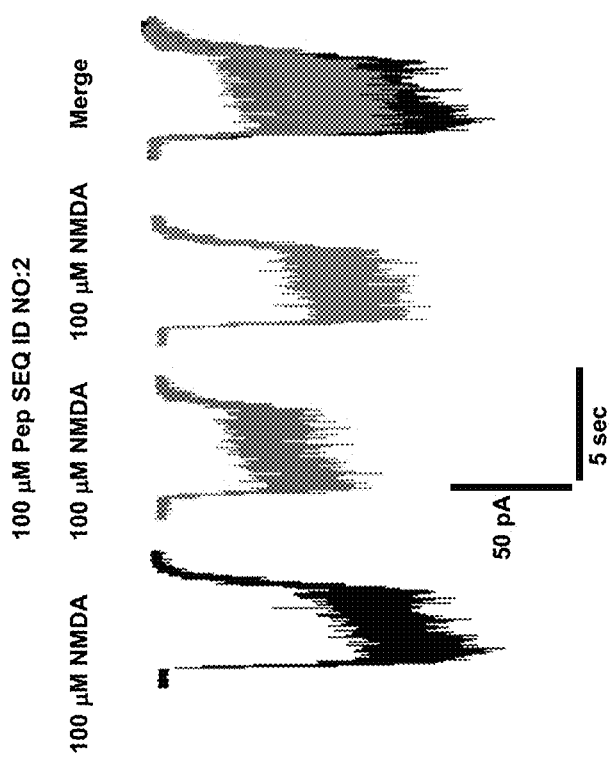
FIGS. 3A, 3B, 3C, 3D, 3E, 3F, 3G and 3H show the effects of peptides having SEQ ID NO: 2 and SEQ ID NO: 3 regarding NMDA receptor-evoked currents on hippocampal neurons.
Figure 3A:
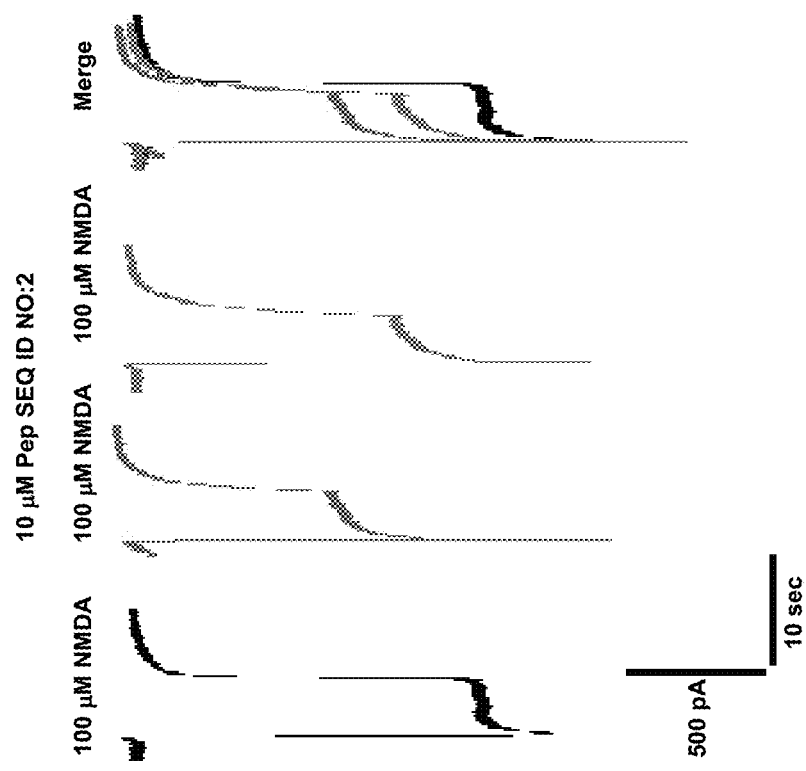
Figure 3D:
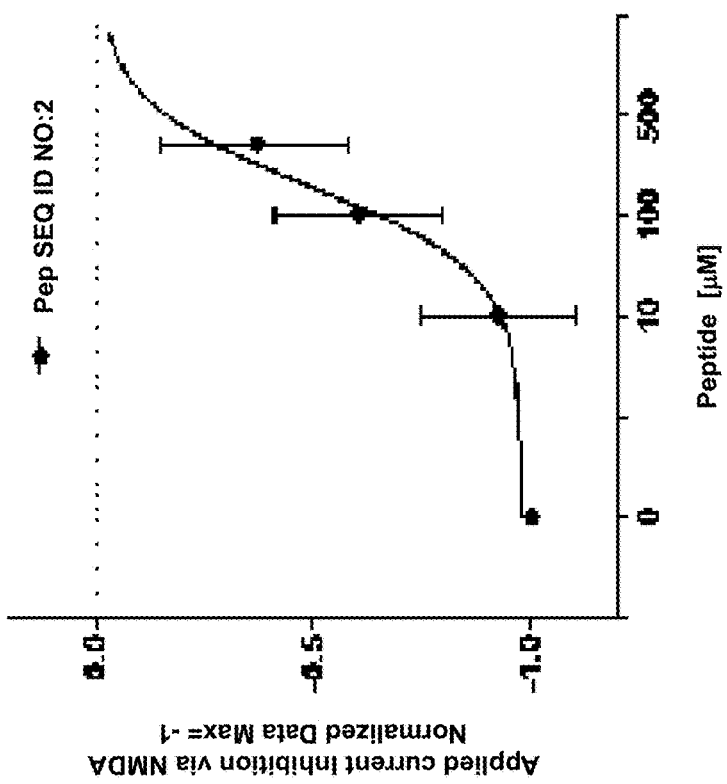
Figure 3C:
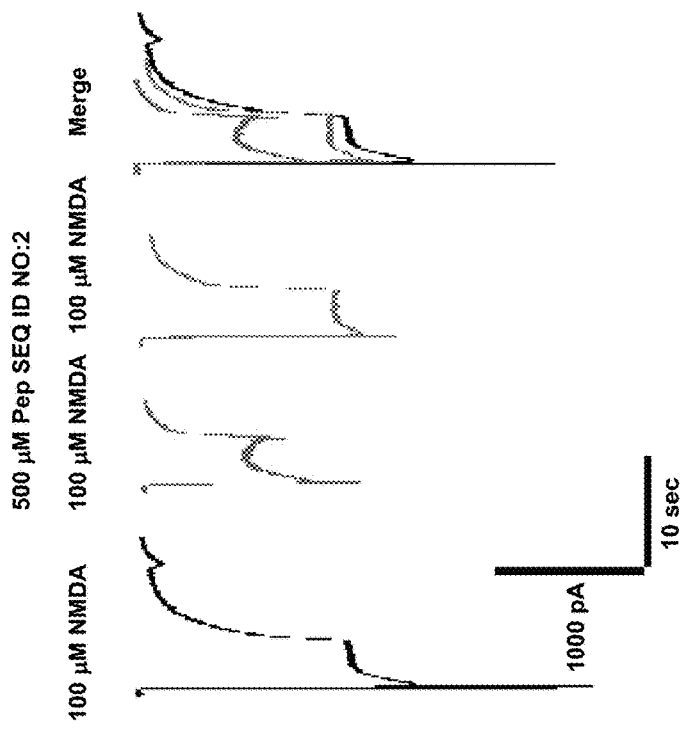
Figure 3F:
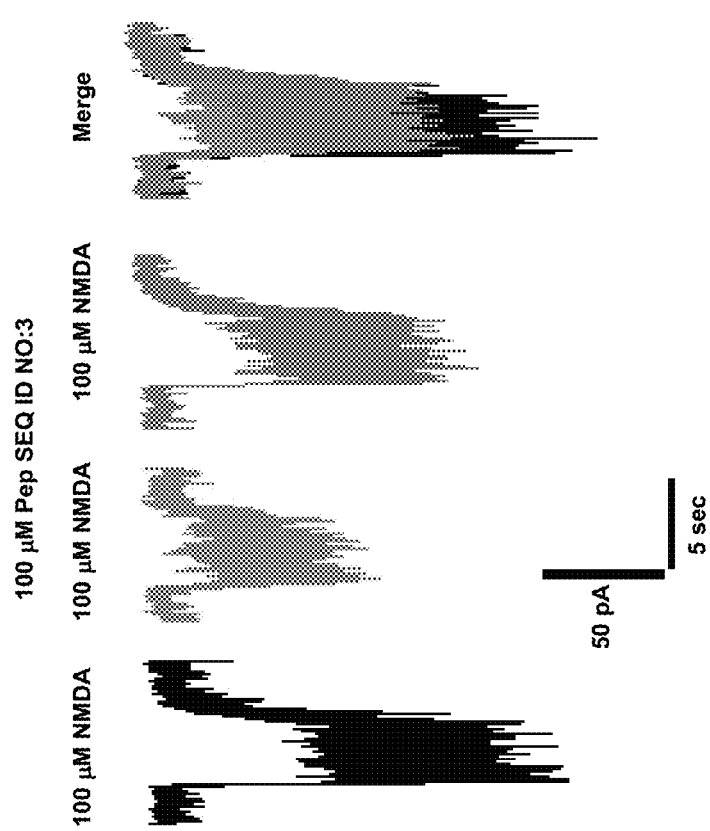
Figure 3E:
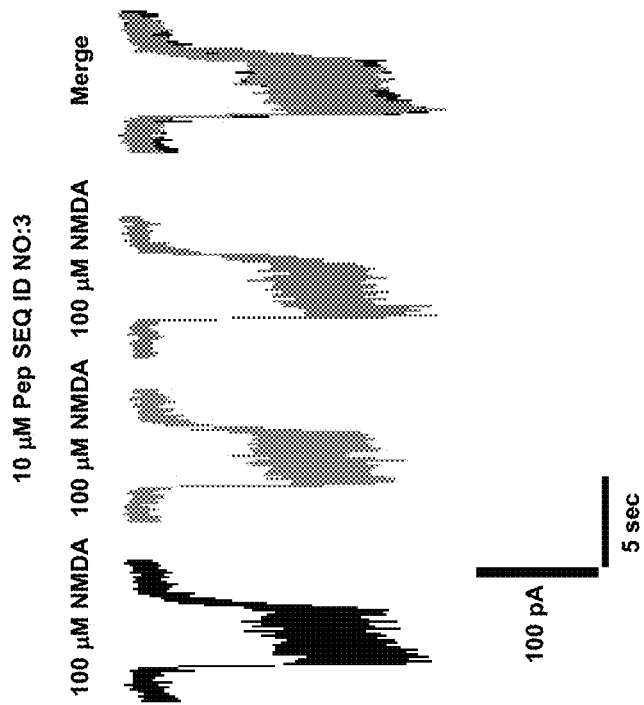

A reduction in current of around 34.75±3.77% (n=7) and 60.75±3.42% (n=11) was observed in NMDA receptor-evoked current when peptide SEQ ID NO: 2 dose was increased from 10 μM to 100 and 500 μM (FIG. 2A) respectively, regarding applications followed by washing and fresh stimulation for NMDA as well as for successive peptide applications, following the dynamics used with the blocker for subunit GluN2B. FIG. 2A shows the application of peptide number 5, illustrating mostly maximum blocking of current at each concentration; FIG. 3 shows current records. A change in receptor kinetics regarding channel closing can observed for 500 μM peptide SEQ ID NO: 2 (FIG. 3C). Regarding the lowest concentrations, there seemed to be competition between the NMDA agonist and the peptides; this could have been indicating that peptide SEQ ID NO: 2 could be a competitive antagonist.

Taking the foregoing data as a whole, it could be said that increasing peptide SEQ ID NO: 2 concentration led to inhibiting NMDA receptor-evoked current and that such inhibition was concentration-dependent; however, according to the dose-response curve values (FIG. 3D) (201.5 μM IC50), it could also be said that peptide SEQ ID NO: 2 did not have high affinity for subunit GluN2B compared to selective antagonists for this subunit in neuron cultures (Conantokin-G $IC_{50}$ 0.5 μM, Klein et al., 1999) and in cultures expressing GluN2B recombinant subunit (Ro25-6981 $IC_{50}$ 0.0090 μM Fischer et al., 1997) and (0.1 μM IC50 for conantokin-G (Teichert et al., 2007). This indicates that γ-carboxyglutamic residues are important for enabling blocking, but not necessary, as peptide SEQ ID NO: 2 (lacking these residues) acted as an agent inhibiting NMDA receptor activity in hippocampal neurons. Something equally important was also observed in most peptide SEQ ID NO: 2 applications as it did not seem to be altering receptor recovery after washing (FIG. 3); something similar happens with most blocking agents acting against this subunit and thus there has been no pharmacological success regarding the treatment of diseases associated with NMDA receptor functioning (Odgen and Traynelis, 2011).

Figure 3H:
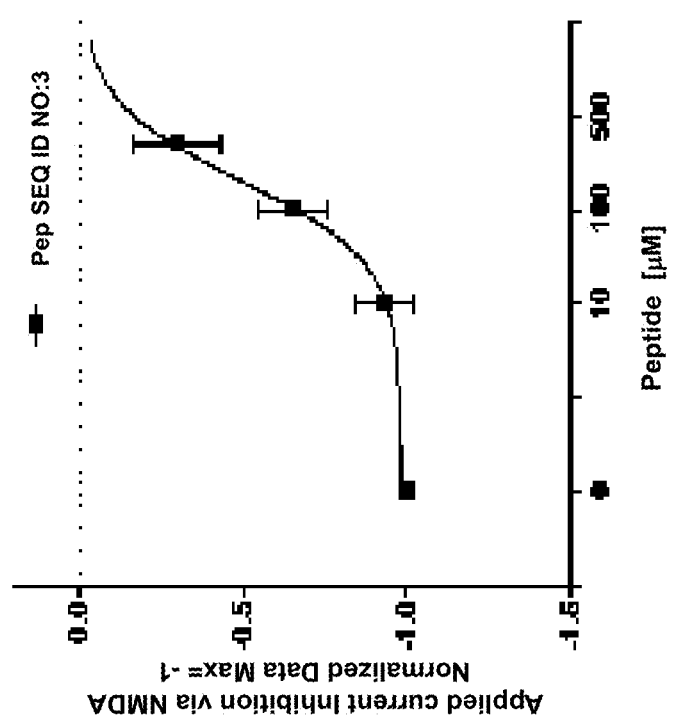
Figure 3G:
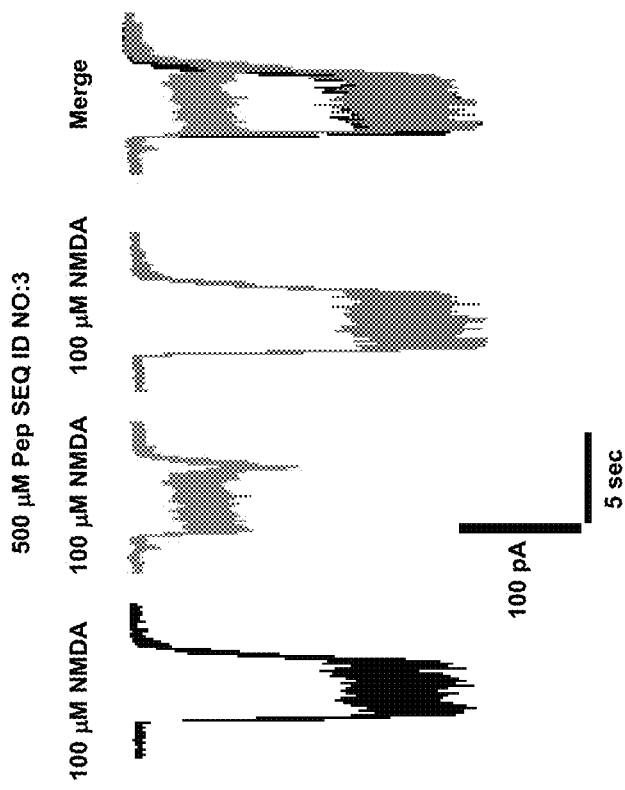

Regarding the other peptide (SEQ ID NO: 3) proposed in this invention, the same methodology was used as that for peptide SEQ ID NO: 2 and it was evaluated at the same concentrations (i.e. 10, 100 and 500 μM) (FIG. 2B). Peptide SEQ ID NO: 3 has two mutations in its amino acid content (sequence) compared to peptide SEQ ID NO: 2, it inhibited 66.5±2.10% (n=6) of the current evoked at 500 μM concentration, 40±2.73% (n=8) at 100 μM concentration and 14±1.35% (n=7) at the lowest proved concentration of 10 μM (FIGS. 3, E, F and G, respectively). Like peptide SEQ ID NO: 2, peptide SEQ ID NO: 3 had a greater degree of recovery following stimulation at high concentration (FIG. 2B). FIG. 3H, shows an estimated 156.3 μM $IC_{50}$ for peptide SEQ ID NO: 3, indicating that it has slightly higher affinity for the NMDA receptor than peptide SEQ ID NO: 2. This would indicate that the residues or amino acids which have become mutated in peptide SEQ ID NO: 2 (i.e. Leu 5 and Asn 8) are important for NMDA receptor-evoked current interaction and inhibition.

NMDA Receptor Recombinant Subunit Expression

Given that peptides SEQ ID NO: 2 and SEQ ID NO: 3 had an inhibitory effect on NMDA receptor-evoked currents in hippocampal neuron primary cultures it was necessary to determine whether peptides SEQ ID NO: 2 and SEQ ID NO: 3 were selective regarding the main NMDA receptor GluN2 subunit subtypes. The GluN2B (NR1a/NR2B) and GluN2A (NR1a/NR2A) subunits coupled to the green fluorescent protein (GFP) were thus expressed in non-neuron HEK293 cells and a functional electrophysiological evaluation was made, following the same methodology described for hippocampal neurons.

Figure 4A:
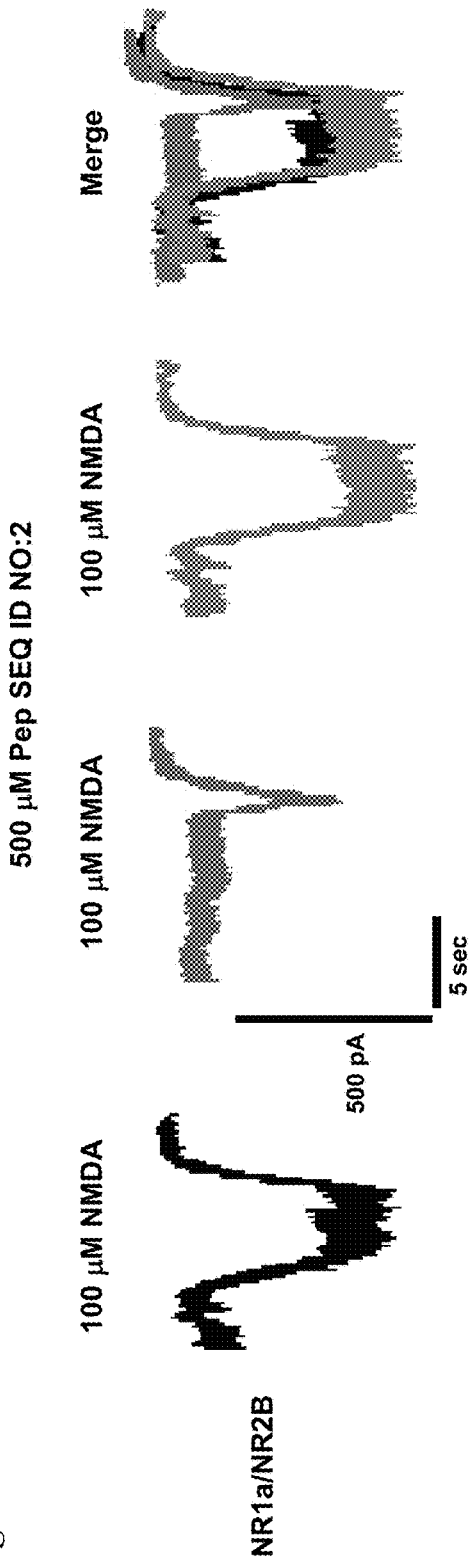
FIGS. 4A and 4B illustrate peptide having SEQ ID NO: 2 selectivity for the NMDA receptor GluN2B subunit. Inhibition of currents evoked by 100 µM NMDA and 10 µM glycine in HEK293 cells expressing subunits NR1a/NR2B is shown in FIG. 4A and NR1a/NR2A is shown in FIG. 4B when using 500 µM peptide having SEQ ID NO: 2. The thick red lines represent the blocking produced by the peptide. The electrophysiological records were made 24 hours after transfection. 3-4 cells were evaluated in each case.
Figure 4B:
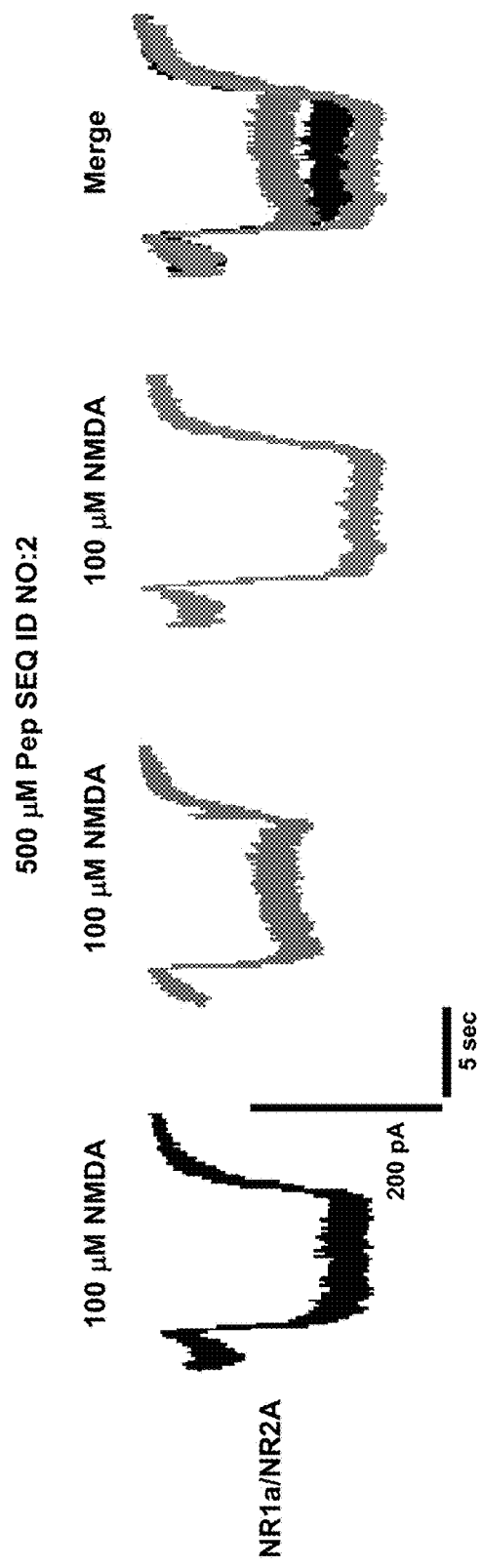

Peptides SEQ ID NO: 2 and SEQ ID NO: 3 were used at the maximum concentration tested in neuron cultures (500 μM). Almost total blocking of the current was observed when using 500 μM of peptide SEQ ID NO: 2 regarding currents evoked from cells expressing recombinant receptor NR1a/NR2B (FIG. 4A) related to current control. A slight reduction in current was observed when the same concentration was evaluated for recombinant NR1a/NR2A (FIG. 4B) regarding that observed for inhibition of recombinant NR1a/NR2B. These results indicated peptide SEQ ID NO: 2 selectivity for subunit GluN2B rather than GluN2A.

Figure 5A:
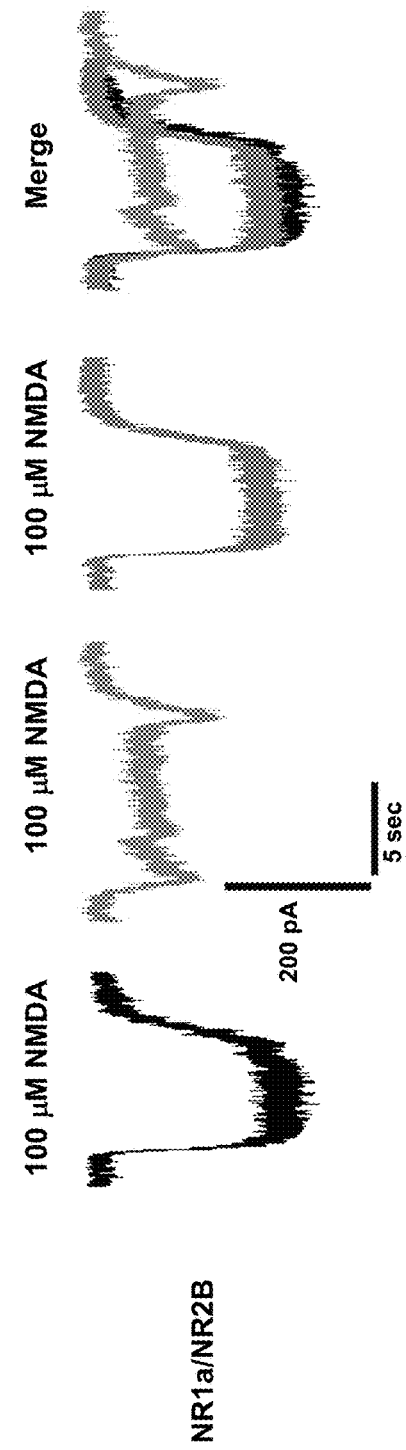
FIGS. 5A and 5B show peptide having SEQ ID NO: 3 selectivity for NMDA receptor recombinant subunits. Inhibiting the currents evoked by 100 µM NMDA and 10 µM glycine in HEK293 cells expressing subunits NR1a/NR2B FIG. 5A and NR1a/NR2A FIG. 5B using 500 µM peptide SEQ ID NO: 3. The thick green lines represent the blocking produced by the peptide. The electrophysiological records were made 24 hours after transfection. 3-4 cells were evaluated in each case.
Figure 5B:
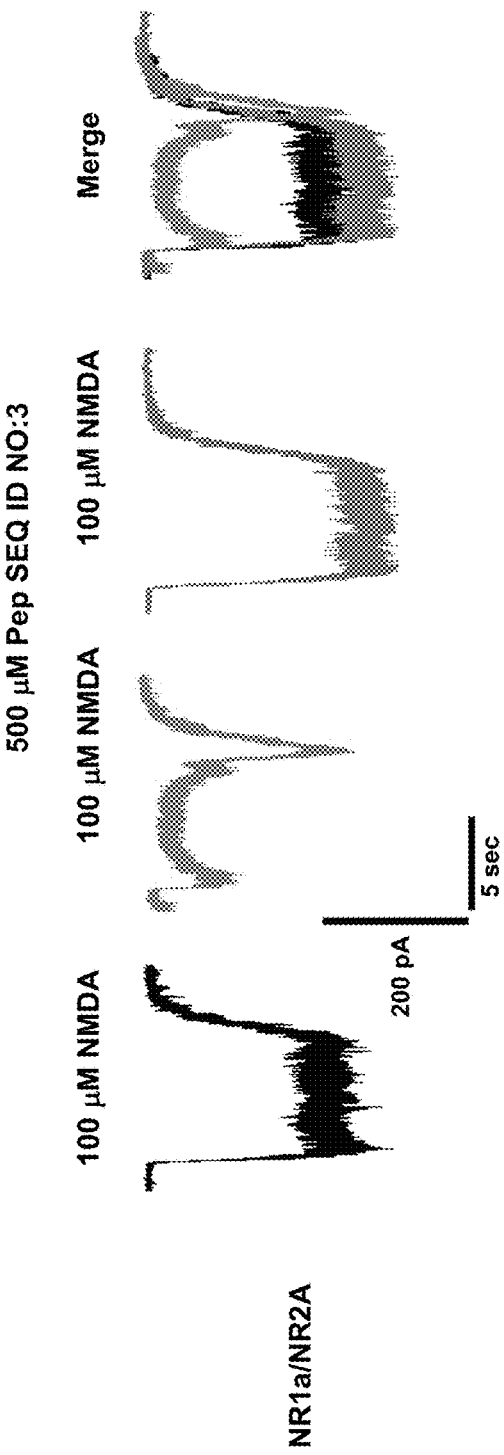

Regarding SEQ ID NO: 3 selectivity for NMDA receptor subunits (see FIG. 5), this peptide at 500 μM concentration inhibited both subunits by more than 50% of maximum current but did not block subunit GluN2B to the same extent as peptide SEQ ID NO: 2, thereby indicating lower affinity and selectivity for this subunit. The GluN2B and GluN2A subunits have a high degree of similarity in their sequences and, given SEQ ID NO: 3 selectivity for GluN2A, it could be thought that mutated amino acids play an important role in interaction with GluN2A. Sheng et al., 2010, analysed a series of conantokin analogues in which one peptide preserved γ-carboxyglutamic residues having the mutations in peptide SEQ ID NO: 3 (i.e. Leu5Tyr and Asn8Ala). Peptide Con-G[L5Y/N8A] was only inhibited by GluN2B subunit subtypes 1a/2B and 1b/2B whereas our results revealed that peptide SEQ ID NO: 3 having L5Y/N8A mutations produced antagonism against both GluN2B and GluN2A, indicating that the Asp residues in this peptide enable a greater range of selectivity.

Figure 6A:
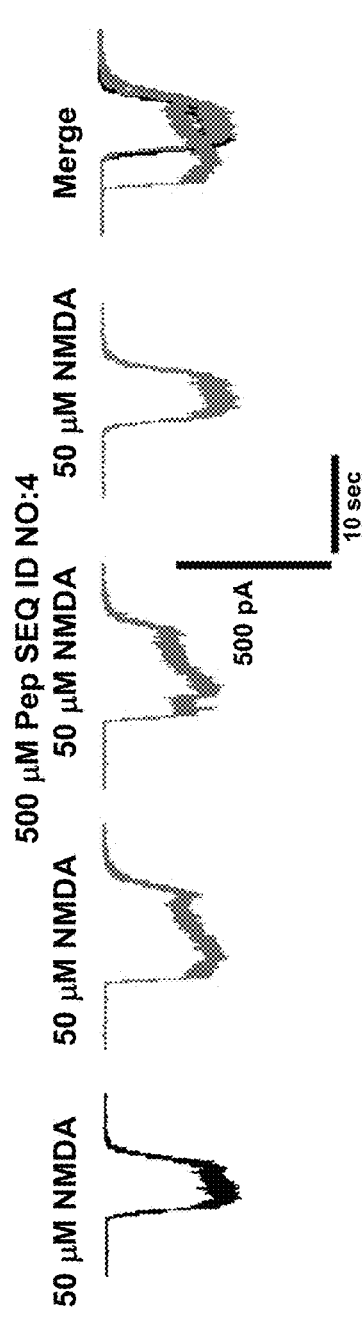
FIGS. 6A and 6B illustrate the peptide having SEQ ID NO: 4 agonist effect on the NMDA receptor.
Figure 6B:
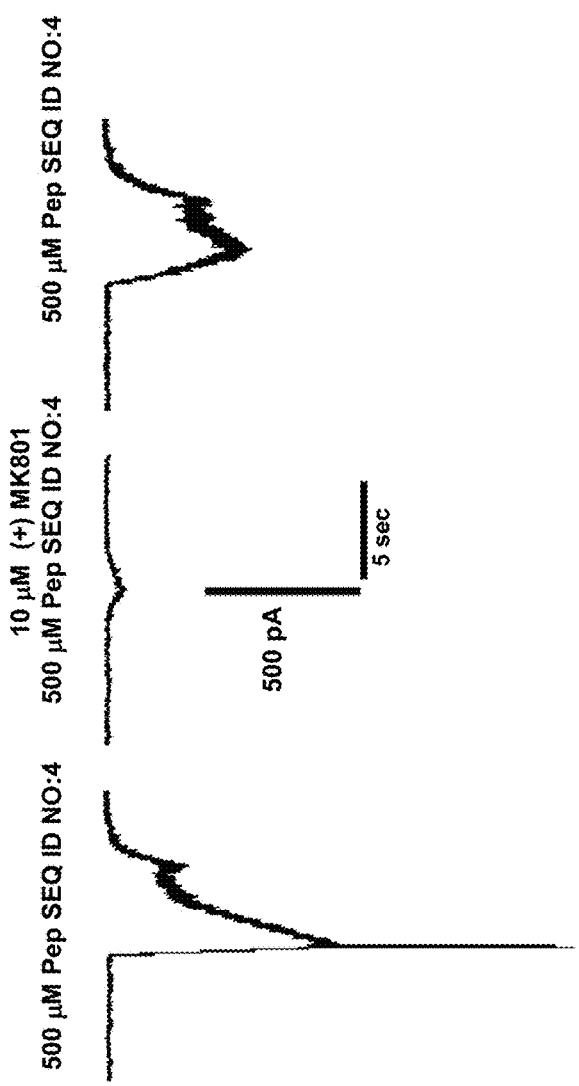

The other peptide presented as SEQ ID NO: 4 in the list of sequences regarding this invention is also 17 amino acids-long, having 90% of the amino acid content of the peptides presented beforehand (i.e. SEQ ID NO: 2 and SEQ ID NO: 3), the difference lying in its sequence having a random order. Functional evaluation of peptide SEQ ID NO: 4 regarding NMDA receptor-evoked currents in hippocampal neurons revealed that this peptide was immediately generating an input current, in addition to the current obtained by stimulation with NMDA (FIG. 6A). A 500 μM pulse was generated from this peptide for 10 seconds to evaluate whether peptide SEQ ID NO: 4, by itself in the absence of the NMDA agonist, was producing any current; interestingly, an input current was found having much greater channel closing kinetics than that seen in this work for NMDA receptor GluN2B subunit current (FIG. 6B). Given the pharmacological treatment used in bath or extracellular solution to enable just NMDA receptor currents to be recorded, the current obtained with peptide SEQ ID NO: 4 should have been NMDA receptor-evoked current. The (+)-MK-801 selective antagonist against the NMDA receptor was thus used to test this. Blocking of more than 90% of input current was found due to stimulation by peptide SEQ ID NO: 4 (FIG. 6, B). This indicated that peptide SEQ ID NO: 4 acting as NMDA receptor agonist.

Much of the pharmaceutical development related to the NMDA receptor has focused on antagonists; however, increased NMDA receptor activity has important therapeutic potential (Lisman et al., 2008). Some study models have shown that the overexpression of some NMDA receptor subunits (mainly GluN2B) could improve learning and memory (Tang et al, 1999, 2001; Cao et al, 2007). Clinical assays involving agonists directed against the NMDA receptor glycine binding site have led to the idea that potentiating the receptor could lead to therapeutic benefits (Heresco-Levy, 2000; Coyle and Tsai, 2004; Shim et al, 2008; Labrie and Roder, 2010).

The peptide in this invention presented as SEQ ID NO: 4, which had an agonist effect, has pharmacological importance regarding regulating NMDA receptor activity concerning memory and learning.

Peptide Synthesis

Peptides presented as SEQ ID NO: 2, SEQ ID NO: 3 and SEQ ID NO: 4 were commercially synthetized. The provider assured a purity of 95-99% using HPLC-MS analysis. Peptides were delivered lyophilized and kept at −20° C. Before the tests, peptides were dissolved into water according their profiles and kept at −20° C.

Biological Examples

Hippocampal Neuron Primary Culture of E18 Sprague Dawley Rat Embryos Having 18 Days Gestation Primary cultures of hippocampal neurons were prepared from Sprague Dawley rat 18 day-old embryos (250-300 g). All the animals were used according to the New York University's Langone Medical Centre Institutional Animal Care and Use Committee's guidelines and correspondence with that entity's ethics committee endorsing the procedures used here. The extraction procedure and culture were based on that reported by Longart et al., 2004 and Beaudoin III et al., 2012.

Extracting the Hippocampi

The rats were sacrificed by inhalation in a CO2 chamber (~10 min, 15 psi), followed by cervical dislocation. The embryos were extracted by caesarean section and placed in cold dissection medium (1× Dulbecco's phosphate-buffered saline (DPBS) (no calcium, no magnesium) (Gibco)) plus 1% penicillin/streptomycin (Gibco)). The embryonic sac was removed from each individual embryo and the embryos were then placed in a Petri dish with cold dissection medium. The skin covering the head and the cranium was stripped off using tweezers and the brain was then freed and the brain-cerebellum extracted whole. The cerebellum was carefully removed; an average of 10-12 brains was collected in cold dissection medium. The cerebral hemispheres were then separated and the meninges removed; once the meninges had been removed the hippocampi could be seen. Using the tweezers carefully, the hippocampi were removed from each hemisphere and transferred to a 15 mL Falcon tube containing 2 mL cold dissection medium.

Hippocampal Cell Dissociation and Culture

The hippocampi were washed twice with 2 mL cold dissection medium. Tissue was dissociated by adding 300 μL 0.25% trypsin (Gibco) to the aforementioned Falcon tube containing 2 mL dissection medium with the hippocampi and incubated at 37° C. for 20 minutes with constant rotation. The trypsin was then inhibited by adding 5 mL complete Neurobasal medium (Neurobasal medium (Gibco) supplemented with 2% B27 (Gibco), 1% penicillin/streptomycin (Gibco) and 0.5 mM GlutaMAX (Gibco)). The previous solution was discarded and two washes were performed, first with 5 mL and then with 10 mL complete Neurobasal medium. The hippocampi were mechanically dissociated in this final volume, using Glass Pasteur pipettes whose tips had been previously fire-polished so as to have three sizes (large, medium and small). Dissociation consisted of passing the hippocampi through the Pasteur pipette tips 10 times per tip, using first the large tip, then the medium followed by the small tip until a cell suspension was obtained. This cell suspension was passed through a filter (Falcon, 70 μm cell strainer) for dissociating target cells from other primary tissue. The trypan blue method was used for cell count and viability on a haemocytometer or in a Neubauer chamber; the cells were sown at 60,000-80,000 cell density per well on 12 mm circular lamella for electrophysiology, after having being coated with a mixture of poly-D-lysine (37.5 μg/ml, Sigma-Aldrich) and laminin (2.5 μg/ml, Invitrogen) in 24-well plates. Some neuron cultures were kept in 500 μL Neurobasal medium (Gibco) supplemented with 2% B27 (Gibco), 1% penicillin/streptomycin and 0.5 mM GlutaMAX (Gibco); B27 was replaced in other cultures by 2% BFS. The cultures were kept at 37° C., 95% humidity, 5% CO2 and half the medium was replaced every 3-4 days. Voltage clamp (whole-cell configuration) electrophysiological records were made, as described in the electrophysiology section, for neurons kept in B27 for 7-20 days in vitro (DIV) and 5-15 DIV for neurons in BFS; 4-11 cells were evaluated for each peptide.

Electrophysiological Records

Electrophysiological (NMDA receptor-evoked current) records were obtained from hippocampal neurons (different DIV) using the patch clamp technique in whole-cell configuration (Hamill et al., 1981; Sackmann and Neher, 1983) with an Axopatch 200B amplifier (Axon Instruments, Binding City, Calif.) and analysed using Clampfit 10.4 software (Axon Instruments, Binding City, Calif.). Membrane potential (voltage clamp) was kept at −60 mV, at room temperature. The neurons were placed in extracellular medium (bath solution) containing 140 mM NaCl, 2.5 mM KCl, 2.0 mM CaCl2, 10 mM HEPES, 10 mM D-glucose, pH 7.4 (Huang et al., 2010).

Magnesium was omitted to prevent voltage-dependent blocking of the NMDA receptor channel (Mayer et al., 1984; Nowak et al., 1984); furthermore, 1 μM tetrodotoxin (Sigma) was added to the extracellular solution, for blocking voltage-dependent Na+ channel activity; 20 μM CNQX (6-cyano-7-nitroquinoxaline-2,3-dione, Sigma) was added to eliminate glutamate AMPA and kainate receptor activity. Additionally, 50 μM bicuculline (Sigma), together with 100 μM picrotoxin (Sigma), were added to eliminate inhibition of GABAA receptor currents and 1 μM strychnine to inhibit glycine channel activity.

The intracellular solution (micropipette) contained 110 mM Cs-gluconate, 20 mM CsCl, 10 mM HEPES, 10 mM EGTA, 4 mM Mg-ATP, 0.4 mM Na-GTP, pH 7.3 (adjusted with CsOH). The borosilicate micropipettes were prepared in a micropipette puller (Sutter Instruments, P-97 mode) and a micro-forge (Narishige, MF-90) and had 1-3 MΩ resistance in extracellular solution. Previously chlorided silver chloride (AgCl) electrodes were used. The cell-attached configuration was used first for making whole-cell records. This involved using a micromanipulator for bringing the pipette as close as possible to the chosen cell when making a recording. Positive pressure was maintained within the micropipette whilst approaching a cell. Gentle negative suction was applied when making contact with the membrane to enable part of the membrane to invaginate into the pipette, thereby provoking firm binding between the membrane and the glass. Moreover, a small depression had to be made in the membrane to enable the micropipette to be pushed lightly against the membrane to ensure an efficient giga-ohm seal (>1 GΩ). Suction through a 1 mL syringe was used to rupture the membrane to ensure electric contact between the recording solution within micropipette and a cell's internal medium.

NMDA receptor-evoked responses were activated by using the NMDA agonist (Sigma) and glycine coagonist (Sigma) against the neurons for 5 seconds and at different concentrations by using a perfusion pencil system. The MK-801 blocker (Sigma) was used for testing NMDA receptor currents and Ro 25-9681 (Sigma), the specific blocker for this subunit, was used for determining NMDA receptor GluN2B subunit currents.

NMDA Receptor Recombinant Subunit Expression cDNA encoding rat NMDA receptor subunits GluN1 (NR1a), GluN2A (NR2A) and GluN2B (NR2B) (each coupled to green fluorescent protein (GFP) and contained in pcDNA3.1, pcDNA1.1 and pRK5 expression vectors, respectively) were bought from Addgene (Cambridge, Mass.). Human embryonic kidney (HEK293) cells were obtained from ATCC (Manassas, Va.) and grown in 25 cm2 flasks in high glucose DMEM medium (Invitrogen) supplemented with heat-inactivated foetal bovine serum (HI-FBS, Invitrogen) and kept at 37° C., 5% CO2 and 95% humidity. Once 100% confluence had been reached (24 hours before transfection), the cells were sown on circular lamella for 24-well plates previously coated with poly-D-lysine (50 ug/ml). The cells were transfected with cDNA encoding NMDA receptor subunits, separately, using lipofectamine 2000 (Invitrogen) in Opti-MEM medium. Transfection ratios were NR1a/NR2A 1:3, NR1a/NR2B 1:3. Half the medium was replaced by complete DMEM three hours after transfection and the cells were kept in 500 μM ketamine for preventing excitotoxicity via NMDA receptor after transfection. Voltage clamp (whole-cell configuration) electrophysiological records were made 24 hours after transfection, as described in the previous section. GFP positive cells were chosen using an Olympus microscope coupled to a fluorescence system; 3-5 cells were evaluated per peptide.

Using the Peptides

The aforementioned perfusion system was used for evaluating the peptides presented in this invention as SEQ ID NO: 2, SEQ ID NO: 3 and SEQ ID NO: 4, separately, and releasing them to the extracellular medium or bath solution.

Each electrophysiological recording lasted 4 minutes; the peptides and agonists and co-agonists (depending on the case) began to be used 30 seconds after starting the recording. Peptide application time was 10 seconds, beginning 5 seconds before 5-second stimulation with the NMDA agonist and glycine coagonist. This was immediately followed by washing or perfusion with bath or extracellular solution to remove the peptides and agonists. Eight recordings were made per cell in most cases, two initial recordings as control involving stimulation with NMDA/glycine, followed by 4 recordings when using the peptides plus NMDA/glycine and two final recordings with just NMDA/glycine for evaluating channel recovery. Each recording was made 4 minutes after the previous one.

All responses were normalised according to the maximum current evoked in the absence of peptides. ClampFit (pClamp10.4) software was used for analysing current amplitude and kinetics; the first 5 or 7 seconds following stimulation were evaluated in some cases.

GraphPad Prism software (V. 5) was used for representing the temporal course of the responses throughout the experiment and adjusting the peptide dose-response curves. Half maximal inhibitory concentration (IC50) levels were calculated, representing the peptide concentration needed for inhibiting 50% of maximum response caused by the agonist. The results are presented as the mean and standard media error (mean±S.E.M). Statistical significance was determined by non-paired t-test when comparing two groups. GraphPad Prism software (V.5) was used for one-way ANOVA Dunnet for comparing three or more groups. Statistically significant differences were considered when $p<0.05$.

Summary

The invention described in this document provides a series of peptides modulating N-methyl-D-aspartate (NMDA) receptor activity. It specifically refers to two synthetic peptides acting as ion inflow antagonists through the NMDA receptor, having NMDA receptor GluN2B and GluN2A subunit specificity, and a peptide having agonist activity regarding the NMDA receptor in rat hippocampal cultures.

REFERENCES

Akazawa C, Shigemoto R, Bessho Y, Nakanishi S, Mizuno N. 1994. Differential expression of five N-methyl-D-aspartate receptor subunit mRNAs in the cerebellum of developing and adult rats. J Comp Neurol. 1; 347(1):150-60.

Alex, A., Saunders G., Dalpe'-Charron, A., Reilly, C., Wilcox, K. 2011. CGX-1007 prevents excitotoxic cell death via actions at multiple types of NMDA receptors. NeuroToxicology 32: 392-399.

Balsara R., Dang A., Donahue D L., Snow T., Castellino F J. 2015. Conantokin-G Attenuates Detrimental Effects of NMDAR Hyperactivity in an Ischemic Rat Model of Stroke. PLoS ONE 10(3):e0122840. doi:10.1371/journal.pone.0122840

Barton M. E., White H. S., Wilcox K. S. 2004. The effect of CGX-1007 and CI-1041, novel nmda receptor antagonists, on NMDA receptor-mediated EPSCs. Epilepsy Res. 59:13-24.

Beaudoin III, Gerard M J, Lee Seung-Hye, Singh Dipika, Yuan Yang, Ng Yu-Gie, Reichardt Louis F & Arikkath Jyothi. 2012. Culturing pyramidal neurons from the early postnatal mouse hippocampus and cortex. Nature Protocols 7, 1741-1754.

Blandl T, Prorok M, Castellino F J. NMDA-receptor antagonist requirements in conantokin-G. FEBS Lett. 1998; 435:257-262.

Cao X, Cui Z, Feng R, Tang Y P, Qin Z, Mei B, and Tsien J Z. 2007 Maintenance of superior learning and memory function in NR2B transgenic mice during ageing. Eur J Neurosci 25:1815-1822.

Chandler P, Pennington M, Maccecchini M L, Nashed N T, Skolnick P. 1993. Polyamine-like actions of peptides derived from conantokin-G, an N-methyl-D-aspartate (NMDA) antagonist. J Biol Chem. August 15; 268(23): 17173-8.

Citri A, Malenka R C. 2008. Synaptic plasticity: multiple forms, functions, and mechanisms. Neuropsychopharmacology. 33(1):18-41.

Coyle J T and Tsai G. 2004. The NMDA receptor glycine modulatory site: a therapeutic target for improving cognition and reducing negative symptoms in schizophrenia. Psychopharmacology (Berl) 174:32-38.

Donevan S D, McCabe R T. 2000. Conantokin G is an NR2B-selective competitive antagonist of N-methyl-D-aspartate receptors. Mol Pharmacol. 58(3):614-23.

Fischer, G., Mutel, V., Trube, G., Malherbe, P., Kew, J. N. C., Mohacsi, E., Heitz, M. P and Kemp, J. A. 1997. Ro 25-6981, a Highly Potent and Selective Blocker of NMethyl-D-aspartate Receptors Containing the NR2B Subunit Characterization in Vitro. JPET 283:1285-1292.

Green, A R. 2002. Why do neuroprotective drugs that are so promising in animals fail in the clinic? An industry perspective. Clin Exp Pharmacol Physiol 29:1030-1034.

Hamill O P, Marty A, Neher E, Sakman B, Sigworth F J. 1981. Improved patch clamp technique for high resolution current recording from cell and cell free membrane patches. Pflügers Arch.; 391:85-100.

Hardingham G E, Bading H. 2010. Synaptic versus extra-synaptic NMDA receptor signalling: implications for neurodegenerative disorders. Nat Rev Neurosci. 11 (10):682-96.

Heresco-Levy U. 2000. N-Methyl-D-aspartate (NMDA) receptor-based treatment approaches in schizophrenia: the first decade. Int J Neuropsychopharmacol 3:243-258.

Hoyte L, Barber P A, Buchan A M, and Hill M D. 2004. The rise and fall of NMDA antagonists for ischemic stroke. Curr Mol Med 4:131-136.

Klein RC1, Galdzicki Z, Castellino F J. 1999. Inhibition of NMDA-induced currents by conantokin-G and conantokin-T in cultured embryonic murine hippocampal neurons. Neuropharmacology. 38(12):1819-29.

Kotermanski S E and Johnson J W (2009) Mg2 imparts NMDA receptor subtype selectivity to the Alzheimer's drug memantine. J Neurosci 29:2774-2779.

Krupp J J, Vissel B, Thomas C G, Heinemann S F, Westbrook G L. 1999. Interactions of calmodulin and alpha-actinin with the NR1 subunit modulate Ca2+-dependent inactivation of NMDA receptors. J Neurosci. February 15; 19(4):1165-78.

Labrie V and Roder J C. 2010. The involvement of the NMDA receptor D-serine/glycine site in the pathophysiology and treatment of schizophrenia. Neurosci Biobehav Rev 34:351-372.

Layer R T, Wagstaff J D, White H S. 2004. Conantokins: peptide antagonists of NMDA receptors. Curr Med Chem. 11 (23): 3073-3084.

Lin C H, Chan F C, Hwang J K, Lyu P C. 1999. Calcium binding mode of gamma-carboxyglutamic acids in conantokins. Protein Eng. July; 12(7):589-95.

Lipton S A. 2006. Paradigm shift in neuroprotection by NMDA receptor blockade: memantine and beyond. Nat Rev Drug Discov. February; 5(2):160-70.

Lisman J E, Coyle J T, Green R W, Javitt D C, Benes F M, Heckers S, and Grace A A. 2008. Circuit-based framework for understanding neurotransmitter and risk gene interactions in schizophrenia. Trends Neurosci 31:234-242.

Lo E H, Dalkara T, and Moskowitz M A. 2003. Mechanisms, challenges and opportunities in stroke. Nat Rev Neurosci 4:399-415.

Longart M, Liu Y, Karavanova I, Buonanno A. 2004. Neuregulin-2 is developmentally regulated and targeted to dendrites of central neurons. J Comp Neurol 472:156-172.

Maccecchini, 1998. U.S. Pat. No. 5,830,998A. Allosteric modulators of the NMDA receptor and their use in the treatment of CNS disorders and enhancement of CNS function.

Maccecchini, 2000. U.S. Pat. No. 6,110,894A. Allosteric modulators of the NMDA receptor and their use in the treatment of CNS disorders and enhancement of CNS function.

Madden, D. 2002. The structure and function of glutamate receptor ion channels. Nat Rev Neurosci, 3(2):91-101.

Mayer M L, Westbrook G L, Guthrie P B. 1984. Voltage-dependent block by Mg2+ of NMDA responses in spinal cord neurones. Nature; 309:261-263.

Mony L, Kew J N, Gunthorpe M J, Paoletti P. 2009a. Allosteric modulators of NR2B-containing NMDA receptors: molecular mechanisms and therapeutic potential. Br J Pharmacol 157:1301-1317.

Monyer H, Burnashev N, dzLaurie D J, Sakmann B, and Seeburg P H. 1994. Developmental and regional expression in the rat brain and functional properties of four NMDA receptors. Neuron 12:529-540.

Muir K W. 2006. Glutamate-based therapeutic approaches: clinical trials with NMDA antagonists. Curr Opin Pharmacol 6:53-60.

Myers R A, McIntosh J M, Imperial J, Williams R W, Oas T, Haack J A, Hernandez J F, Rivier J, Cruz L J and Olivera B M. 1990. Peptides from *Conus* venoms which affect Ca++ entry into neurons. J Toxicol Toxin Rev 9: 179-202.

Nahum-Levy R., Lipinski D., Shavit S., Benveniste M. 2001. Desensitization of NMDA receptor channels is modulated by glutamate agonists. Biophysical Journal.; 80(5):2152-2166.

Nowak L, Bregestovski P, Ascher P, Herbet A, Prochiantz A. 1984. Magnesium gates glutamate-activated channels in mouse central neurones. Nature; 307:462-465.

Ogden K K, Traynelis S F. 2011. New advances in NMDA receptor pharmacology. Trends Pharmacol Sci. December; 32(12):726-33.

Olivera B M. 1997. *Conus* venom peptides, receptor and ion channel targets and drug design: 50 million years of neuropharmacology. Mol Biol Cell 8:2101-2109

Parsons C G, Danysz, W and Lodge D. 2002. Introduction to glutamate receptors, their function and pharmacology, in Ionotropic Glutamate Receptors as Therapeutic Targets (Danysz W, Lodge D, and Parsons C G eds) pp 1-30, F. P. Graham Publishing Co., Johnson City, Tenn.

Prorok M and Castellino F J. 2007. The molecular basis of conantokin antagonism of NMDA receptor function. Current Drug Targets 8:633-642.

Renzhan Hong et al., 2011. Patent, CN102167729A. Conotoxin analog Glu-Con-G (Glutamate-Conantokin-G) with morphine-dependent resistance and analgesic effect.

Sacco R L, DeRosa J T, Haley E C Jr, Levin B, Ordronneau P, Phillips S J, Rundek T, Snipes R G, Thompson J L, and Glycine Antagonist in Neuroprotection Americas Investigators. 2001. Glycine antagonist in neuroprotection for patients with acute stroke: GAIN Americas: a randomized controlled trial. JAMA 285:1719-1728.

Sackmann, B. and Neher, E. (ed.).1983. Single channel recording. New York. Plenum Press.

Saydoff et al., 1998. Patent CA 2288346 A1. Use of conantokins for producing analgesia or for neuroprotection.

Sheng Zhenyu, Prorok Mary, and. Castellino Francis J. 2010. Specific determinants of conantokins that dictate their selectivity for the NR2B subunit of N-methyl-D-aspartate receptors. Neuroscience. October 27; 170(3): 703-10.

Shim S S, Hammonds M D, and Kee B S. 2008. Potentiation of the NMDA receptor in the treatment of schizophrenia: focused on the glycine site. Eur Arch Psychiatry Clin Neurosci 258:16-27.

Small D L and Tauskela J S. 2005. Glutamate receptor pharmacology: lessons learned from the last decade of stroke trials, in Glutamate Receptors in Peripheral Tissue: Excitatory Transmission outside the CNS (Gill S and Pulido O eds) pp 27-45, Kluwer Academic/Plenum Publishers, New York.

Sobolevsky A I, Rosconi M P, and Gouaux E. 2009. X-ray structure, symmetry and mechanism of an AMPA-subtype glutamate receptor. Nature 462:745-756.

Tang Y P, Shimizu E, Dube G R, Rampon C, Kerchner G A, Zhuo M, Liu G, and Tsien J Z. 1999. Genetic enhancement of learning and memory in mice. Nature 401: 63-69.

Tang Y P, Wang H, Feng R, Kyin M, and Tsien J Z. 2001. Differential effects of enrichment on learning and memory function in NR2B transgenic mice. Neuropharmacology 41:779-790.

Teichert R W, Jimenez E C, Twede V, Watkins M, Hollmann M, Bulaj G, and Olivera B M. 2007. Novel conantokins from *Conus parius* venom are specific antagonists of N-methyl-D-aspartate receptors. J Biol Chem 282:36905-36913.

Traynelis, Stephen F., Wollmuth., L P., Chris J. McBain, Frank S. Menniti, Katie M. Vance, Kevin K. Ogden, Kasper B. Hansen, Hongjie Yuan, Scott J. Myers, and Ray Dingledine. 2010. Glutamate Receptor Ion Channels: Structure, Regulation, and Function. Pharmacol Rev 62:405-496.

Wang C X and Shuaib A. 2005. NMDA/NR2B selective antagonists in the treatment of ischemic brain injury. Curr Drug Targets CNS Neurol Disord 4:143-151.

Warder, S. E., Prorok, M., Chen, Z., Li, L., Zhu, Y., Pedersen, L. G., Ni, F., and Castellino, F. J. 1998. The roles of individual gamma-carboxyglutamate residues in the solution structure and cation-dependent properties of conantokin-T. J. Biol. Chem. 273, 7512-7522.

Waxman, E and Linch, D. 2005. N-Methyl-D-aspartate Receptor Subtype Mediated Bidirectional Control of p38 Mitogen-activated Protein Kinase. The Journal of Biological Chemistry. Vol. 280, No. 32, Issue of August 12, pp. 29322-29333.

Williams A J, Dave J R, Lu X M, Ling G, Tortella F C. 2002. Selective NR2B NMDA receptor antagonists are protective against staurosporine-induced apoptosis. Eur J Pharmacol; 452(1):135-6.

Wong E H, Kemp J A, Priestley T, Knight A R, Woodruff G N, Iversen L L. 1986. The anticonvulsant MK-801 is a potent N-methyl-D-aspartate antagonist. Proc Natl Acad Sci USA. September; 83(18):7104-8.

Xiao C, Huang Y, Dong M, Hu J, Hou S, Castellino F J, Prorok M, Dai Q. 2008. NR2B-selective conantokin peptide inhibitors of the NMDA receptor display enhanced antinociceptive properties compared to non-selective conantokins. Neuropeptides. 42:601-609.

Yurkewicz L, Weaver J, Bullock M R, and Marshall L F. 2005. The effect of the selective NMDA receptor antagonist traxoprodil in the treatment of traumatic brain injury. J Neurotrauma 22:1428-1443.

Zhou, L. M., Szendrei, G. I., Fossom, L. H., Maccecchini, M. L., Skolnick, P., and Otvos, L., Jr. 1996. Synthetic analogues of conantokin-G. NMDA antagonists acting through a novel polyamine-coupled site. J. Neurochem. 66, 620-628

PATENT REFERENCES

US2012083449 (A1); U.S. Pat. No. 8,536,129 (B2) U.S. Pat. No. 7,846,897 (B2); US2009131321 (A1) U.S. Pat. No. 5,804,550 (A); U.S. Pat. No. 8,003,609 (B2); US2007059320 (A1) US2007042969 (A1); U.S. Pat. No. 6,110,894 (A); WO9907413 (A1) WO9743306 (A1); WO2004045535 (A2); WO2004045535 (A3); CA 2288346 A1; U.S. Pat. No. 5,830,998A; 6,110,894A; CN102167729A

What is claimed is:

1. An artificially designed peptide having antagonist activity against the NMDA receptor, wherein said peptide consists of the amino acid sequence KLGMRSELQIDNDQDAD (SEQ ID NO: 4).

2. An artificially designed peptide acting as a membrane ionic permeability modifier in cell cultures and as a membrane ionic permeability modifier of neurons in a primary culture; wherein said peptide consists of the amino acid sequence KLGMRSELQIDNDQDAD (SEQ ID NO: 4).

3. A pharmaceutical composition comprising the peptide of claim 1, and a pharmaceutically acceptable carrier or vehicle.

4. A pharmaceutical composition comprising the peptide of claim 2, and a pharmaceutically acceptable carrier or vehicle.

* * * * *

```
                           SEQUENCE LISTING

<160> NUMBER OF SEQ ID NOS: 4

<210> SEQ ID NO 1
<211> LENGTH: 17
<212> TYPE: PRT
<213> ORGANISM: Conus geographus
<220> FEATURE:
<221> NAME/KEY: MOD_RES
<222> LOCATION: (1)..(17)
<223> OTHER INFORMATION: GAMMA-CARBOXYGLUTAMIC ACID HYDROXYLATION
      Xaa at positions 3, 4, 7, 10 and 14 is replaced by Asp

<400> SEQUENCE: 1

Gly Glu Xaa Xaa Leu Gln Xaa Asn Gln Xaa Leu Ile Arg Xaa Lys Ser
1               5                   10                  15

Asn

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Gly Glu Asp Asp Leu Gln Asp Asn Gln Asp Leu Ile Arg Asp Lys Ser
1               5                   10                  15

Asn

<210> SEQ ID NO 3
<211> LENGTH: 17
<212> TYPE: PRT
<213> ORGANISM: Artificial Sequence
<220> FEATURE:
<223> OTHER INFORMATION: Synthetic

<400> SEQUENCE: 3

Gly Glu Asp Asp Tyr Gln Asp Ala Gln Asp Leu Ile Arg Asp Lys Ser
1               5                   10                  15

Asn

<210> SEQ ID NO 4
<211> LENGTH: 17
<212> TYPE: PRT
<213> ORGANISM: Artificial Sequence
<220> FEATURE:
<223> OTHER INFORMATION: Synthetic

<400> SEQUENCE: 4

Lys Leu Gly Met Arg Ser Glu Leu Gln Ile Asp Asn Asp Gln Asp Ala
1               5                   10                  15

Asp
```